United States Patent
Giraud et al.

(10) Patent No.: US 10,492,980 B2
(45) Date of Patent: Dec. 3, 2019

(54) MASSAGE DEVICE WITH AT LEAST ONE MASSAGE HEAD HAVING ECCENTRIC ROTATION

(71) Applicant: SEB S.A., Ecully (FR)

(72) Inventors: Camille Giraud, Lyons (FR); Régis Fereyre, Chavanay (FR); Laurence Laranjeira, Moidieu Detourbe (FR); Franck Mandica, Francheville (FR)

(73) Assignee: SEB S.A. (FR)

( * ) Notice: Subject to any disclaimer, the term of this patent is extended or adjusted under 35 U.S.C. 154(b) by 859 days.

(21) Appl. No.: 15/029,268

(22) PCT Filed: Oct. 15, 2014

(86) PCT No.: PCT/FR2014/052632
§ 371 (c)(1),
(2) Date: Apr. 14, 2016

(87) PCT Pub. No.: WO2015/055955
PCT Pub. Date: Apr. 23, 2015

(65) Prior Publication Data
US 2016/0256348 A1 Sep. 8, 2016

(30) Foreign Application Priority Data
Oct. 17, 2013 (FR) ...................................... 1360118

(51) Int. Cl.
*A61H 15/00* (2006.01)
*A61H 15/02* (2006.01)
(Continued)

(52) U.S. Cl.
CPC ......... *A61H 15/0085* (2013.01); *A61H 15/00* (2013.01); *A61H 15/02* (2013.01);
(Continued)

(58) Field of Classification Search
CPC ................ A61H 7/005; A61H 23/0254; A61H 15/0085; A61H 15/02; A61H 2205/022;
(Continued)

(56) References Cited

U.S. PATENT DOCUMENTS 1,173,838 A * 2/1916 Miller ................ A61H 15/0085
601/113
1,777,151 A * 9/1930 Ruttger-Pelli ......... A61H 15/00
601/113
(Continued)

FOREIGN PATENT DOCUMENTS

CA 2476560 A1 * 8/2005 ............. A61H 15/00
FR 2900329 A1 11/2007
WO 97/22326 A1 6/1997

*Primary Examiner* — Tu A Vo
(74) *Attorney, Agent, or Firm* — The Webb Law Firm

(57) ABSTRACT

Provided is a facial massage device including: a massage head (1) that includes: a bearing element (20) that forms a bearing ring (21) defining a bearing surface (S) lying within a bearing plane (P) and a working area (Z) located within the bearing ring, within the bearing ring and inside the working area (Z), at least one working head (22) that has a working surface that extends, protruding, from the bearing plane (P), maneuvering device (25) designed to move each working head (22) in rotation about at least one axis of rotation (Δ, Δ') offset relative to the centre of the corresponding working surface (T), and a drive housing that carries the massage head (1) and that includes an electric motor (6) that actuates drive means (7) designed to transmit the drive from the electric motor (6) to the maneuvering device (25).

28 Claims, 3 Drawing Sheets

(51) Int. Cl.
*A61N 5/06* (2006.01)
*A61N 1/32* (2006.01)
*A61M 35/00* (2006.01)

(52) U.S. Cl.
CPC ...... *A61N 5/0616* (2013.01); *A61H 2015/005* (2013.01); *A61H 2015/0007* (2013.01); *A61H 2015/0042* (2013.01); *A61H 2015/0064* (2013.01); *A61H 2201/0107* (2013.01); *A61H 2201/0153* (2013.01); *A61H 2201/0157* (2013.01); *A61H 2201/105* (2013.01); *A61H 2201/1215* (2013.01); *A61H 2201/1472* (2013.01); *A61H 2201/1671* (2013.01); *A61H 2201/1685* (2013.01); *A61H 2205/022* (2013.01); *A61M 35/003* (2013.01); *A61N 1/328* (2013.01); *A61N 2005/0644* (2013.01)

(58) Field of Classification Search
CPC .... A61H 2201/1207; A61H 2201/5025; A61H 2201/1472; A61H 2201/0188; A61H 2201/1215; A61H 2015/0064; A61H 2201/1685; A61H 2201/1692; A61H 2201/10; A61H 2201/105; A46B 15/0036; A46B 2200/102; A61N 5/0616; A61N 2005/0666; A61N 2005/0662; A61N 2005/0652; A61N 2005/0644; A61N 2005/0659; A61B 2017/00734; A61B 2017/00747
See application file for complete search history.

(56) References Cited

U.S. PATENT DOCUMENTS

| | | | | |
|---|---|---|---|---|
| 2,034,758 A * | 3/1936 | Hicke, Jr. | ........ | A61H 15/0085 601/113 |
| 2,043,114 A * | 6/1936 | Ruttger-Pelli | ........ | A61H 15/00 601/113 |
| 3,994,290 A * | 11/1976 | Springer | ........ | A61H 15/0078 601/131 |
| 4,526,163 A * | 7/1985 | Fedders | ........ | A61H 7/004 601/112 |
| 4,858,600 A * | 8/1989 | Gross | ........ | A61H 15/0085 601/159 |
| 5,105,802 A * | 4/1992 | Pokorny | ........ | A61H 15/0085 601/131 |
| 5,662,593 A * | 9/1997 | Tillman | ........ | A61H 15/0085 601/113 |
| 5,685,827 A * | 11/1997 | Shimizu | ........ | A61H 15/0085 601/112 |
| 5,725,483 A * | 3/1998 | Podolsky | ........ | A46B 13/04 601/113 |
| 5,797,859 A * | 8/1998 | Prehodka | ........ | A61H 7/004 601/113 |
| 6,632,186 B2 * | 10/2003 | Tsai | ........ | A61H 15/0085 601/112 |
| 6,979,302 B2 * | 12/2005 | Chen | ........ | A61H 7/005 601/112 |
| 7,427,274 B2 * | 9/2008 | Harris, Jr. | ........ | A61H 7/004 601/15 |
| 8,088,085 B2 * | 1/2012 | Thiebaut | ........ | A61H 7/003 601/112 |
| 2003/0125648 A1 | 7/2003 | Leason et al. | | |
| 2005/0209538 A1 * | 9/2005 | Lev | ........ | A61H 15/0078 601/15 |
| 2008/0014011 A1 * | 1/2008 | Rossen | ........ | A45D 34/041 401/195 |
| 2008/0183252 A1 | 7/2008 | Khen | | |
| 2008/0262394 A1 * | 10/2008 | Pryor | ........ | A61H 7/007 601/15 |
| 2009/0306559 A1 * | 12/2009 | Tsai | ........ | A61H 7/007 601/128 |
| 2010/0069800 A1 * | 3/2010 | Hsu | ........ | A61H 15/02 601/112 |
| 2010/0081973 A1 * | 4/2010 | Tsai | ........ | A61H 15/0078 601/134 |
| 2010/0160841 A1 | 6/2010 | Wu | | |
| 2010/0179460 A1 * | 7/2010 | Tsai | ........ | A61H 7/004 601/134 |
| 2010/0280426 A1 * | 11/2010 | Tsai | ........ | A61H 15/0078 601/99 |
| 2010/0286577 A1 * | 11/2010 | Tsai | ........ | A61H 15/0078 601/112 |
| 2011/0009783 A1 * | 1/2011 | Dverin | ........ | A61B 18/14 601/137 |

* cited by examiner

MASSAGE DEVICE WITH AT LEAST ONE MASSAGE HEAD HAVING ECCENTRIC ROTATION

CROSS-REFERENCE TO RELATED APPLICATIONS

This is the United States national phase of International Application No. PCT/FR2014/052632 filed Oct. 15, 2014, and claims priority to French Patent Application No. 1360118 filed Oct. 17, 2013,the disclosures of which are hereby incorporated in their entirety by reference.

Field of the Invention

The present invention relates to the field of devices for the treatment of skin, in particular facial skin. The device according to the invention makes it possible, at the very least, to massage the skin in order to tone it. The massage device according to the invention will be used by people desiring to look good by remodeling, firming, and rejuvenating their skin, in particular their facial skin.

Description of Related Art

Skin massage devices are generally composed of a body equipped with motor means and a massage head that comprises massage elements configured to be activated under the action of the motor means, by means of a transmission mechanism. Patent Application US 20100160841 proposed a body in the shape of a pistol grip, on which it is possible to fit a massage head comprising five working heads rigidly connected to a plate that turns about an eccentric axis of rotation.

While such massage devices make it possible to massage large-area regions of the body, they are not designed for massaging delicate, small-area regions that may also have a small curvature radius, as is the case for the face. This gave rise to the need for a massage device that is better designed for a facial massage than those of the prior art.

SUMMARY OF THE INVENTION

In order to achieve this objective, the invention relates to a facial massage device comprising:
  a massage head that comprises:
    a bearing element that is intended to be placed against the face and that forms a bearing ring defining a bearing surface lying within a bearing plane on the one hand, and a working zone located within the bearing ring on the other hand,
  within the bearing ring and inside the working zone, at least one working head that has a working surface that extends, protruding, from the bearing plane, maneuvering means designed for moving each working head in rotation about at least one axis of rotation offset relative to the center of the corresponding working surface,
  and a drive housing that carries the massage head and that comprises an electric motor actuating drive means designed for transmitting the movement of the electric motor to the maneuvering means.

The design of the massage head of the device according to the invention is well-suited for massaging small regions such as those of the face. Indeed, the bearing surface tones the skin tone by delimiting the region of the massage such that the action of each working head is concentrated on the region of skin located within the bearing surface.

According to a feature of the invention, the bearing surface is composed of a first material and each working surface is composed of a second material with a rigidity different than that of the first material, the first material and the second material being chosen from among:
  a rigid material that is non-deformable under a manual force,
  a material that is elastically deformable under a manual force.

By using two materials of different rigidities for the bearing surface and the working surface or surfaces, the action of the bearing surface can be effectively decoupled from that of the working surface or surfaces.

According to a variant of this feature, the working surface is composed of an elastically deformable material. This elastically deformable nature of the working surface ensures comfortable contact with the user's skin and adaptation to the morphology of the region being massaged.

According to a feature of the invention, each working surface has a convex shape. This feature ensures an effective massage that is neither unpleasant nor painful.

Advantageously, each working surface has an essentially spherical shape and extends, permanently protruding, from the bearing plane by a height that, measured between the top of the working surface and the bearing plane, is equal or greater than the curvature radius of the working surface. According to the invention, this protrusion height can be constant or variable during the massage.

According to another feature of the invention, each working head comprises a ball that forms the corresponding working surface. The utilization of a massage ball makes it possible to provide an essentially spherical working surface.

According to a variant of this feature, each ball is movable in rotation on itself. This rotation can be free, thus allowing the working surface to roll on the skin, or it can be controlled by maneuvering means so as to stimulate the skin in a specific way.

According to a feature of the invention, each working surface is rigid.

According to another feature of the invention, each working surface is smooth.

According to still another feature of the invention, each working surface is metal. This feature makes it possible to create, for example, a cool sensation during skin contact.

According to a variant of this feature of the invention, each working surface is made of a material having a hardness of between 20 and 70 shore.

According to an embodiment of the invention, the massage device according to the invention comprises a single working head, the center of which is offset relative to the center of the working zone.

According to a variant of this feature, the center of the working head is offset relative to the center of the working zone by a distance greater than or equal to ⅙ of the smallest dimension of the working zone and less than half of the smallest dimension of the working zone.

According to another embodiment of the invention, the massage device comprises at least two working heads, the center of which is offset relative to the center of the working zone.

According to a variant of this embodiment, the maneuvering means are designed to move each working head in rotation about an axis of rotation that is offset relative to the center of the corresponding working surface and separate from the axis of rotation of the other working head or heads. According to this variant, each working head will thus have its own movement in rotation.

According to a feature of the invention, the bearing element is hollow and rigid. The rigid nature of the bearing element is understood to mean the fact that the bearing element does not deform under a manual application force on the skin. This feature makes it possible to control the protrusion height of each working surface relative to the bearing plane defined by the bearing surface carried by the bearing element. In the case in which the bearing surface is made of a flexible material, the latter will be preferably chosen such that its deformation will induce a variation of the position of the bearing plane of less than a few millimeters and preferably less than 2 mm.

According to a feature of the invention, the massage device comprises means of applying an electric current that comprise at least one electrode that is intended to contact the skin and that is connected to a unit for generating an electric current and/or voltage. The utilization of such an electrode makes it possible to induce, for example, micro-currants in the skin, electrostimulation of the muscles, or even electrophoresis phenomena that enhance the penetration of active principles applied to the skin before and/or during the massage.

According to a variant of this feature, at least the support element or the working head carries at least one electrode.

According to an embodiment of the invention, the massage device comprises means for diffusing light toward the face. The utilization of such light diffusion means makes it possible to effect a phototherapy treatment and/or activate active principles applied to the skin before and/or during the massage.

According to a feature of this embodiment, the light diffusion means comprise at least one light source and at least one optical diffusion system comprising an outlet side intended to be oriented toward the face.

According to a variant of this feature, at least the bearing element or the working head comprise a light outlet side.

According to a variant, at least the bearing element or the working head is at least partially transparent.

According to another embodiment of the invention, the massage device comprises cosmetic product application means. The utilization of such application means makes it possible to deposit a cosmetic product on the skin before and/or during the massage.

According to a feature of this embodiment, the cosmetic product application means comprise at least one cap, which comprises a plug that is saturated with cosmetic product and that is removably fitted on the bearing element and/or the working head.

According to another feature of this embodiment, the cosmetic product application means comprise a cosmetic product container and at least one dispensing nozzle connected to a system for extracting the product in the container, for instance a pump.

According to still another feature of this embodiment, the cosmetic product application means comprise at least one dispensing nozzle located in the working head or in the bearing element.

According to a feature of the invention, the massage head is removably fitted on the drive housing. The removable nature of the massage head permits a plurality of interchangeable massage heads to be used with the same housing.

According to a variant of this feature, the massage head comprises identification means and the drive housing comprises means for recognizing the identification means that are connected to a control unit designed for controlling the functioning of the massage device on the basis of the recognized massage head. The utilization of such an identification system enables the automatic adjustment of the functioning of the massage device, thus relieving the user of this task.

Obviously the different features, variants, and embodiments of the invention can be used in diverse combinations with one another, as they are neither mutually incompatible nor mutually exclusive.

Furthermore, diverse other features of the invention emerge from the appended description, which refers to the drawings that illustrate non-limiting embodiments of a massage device according to the invention.

DETAILED DESCRIPTION OF THE INVENTION

It should be noted that the structural and/or functional elements common to the different embodiments in these figures may have the same reference signs.

Figure 1:
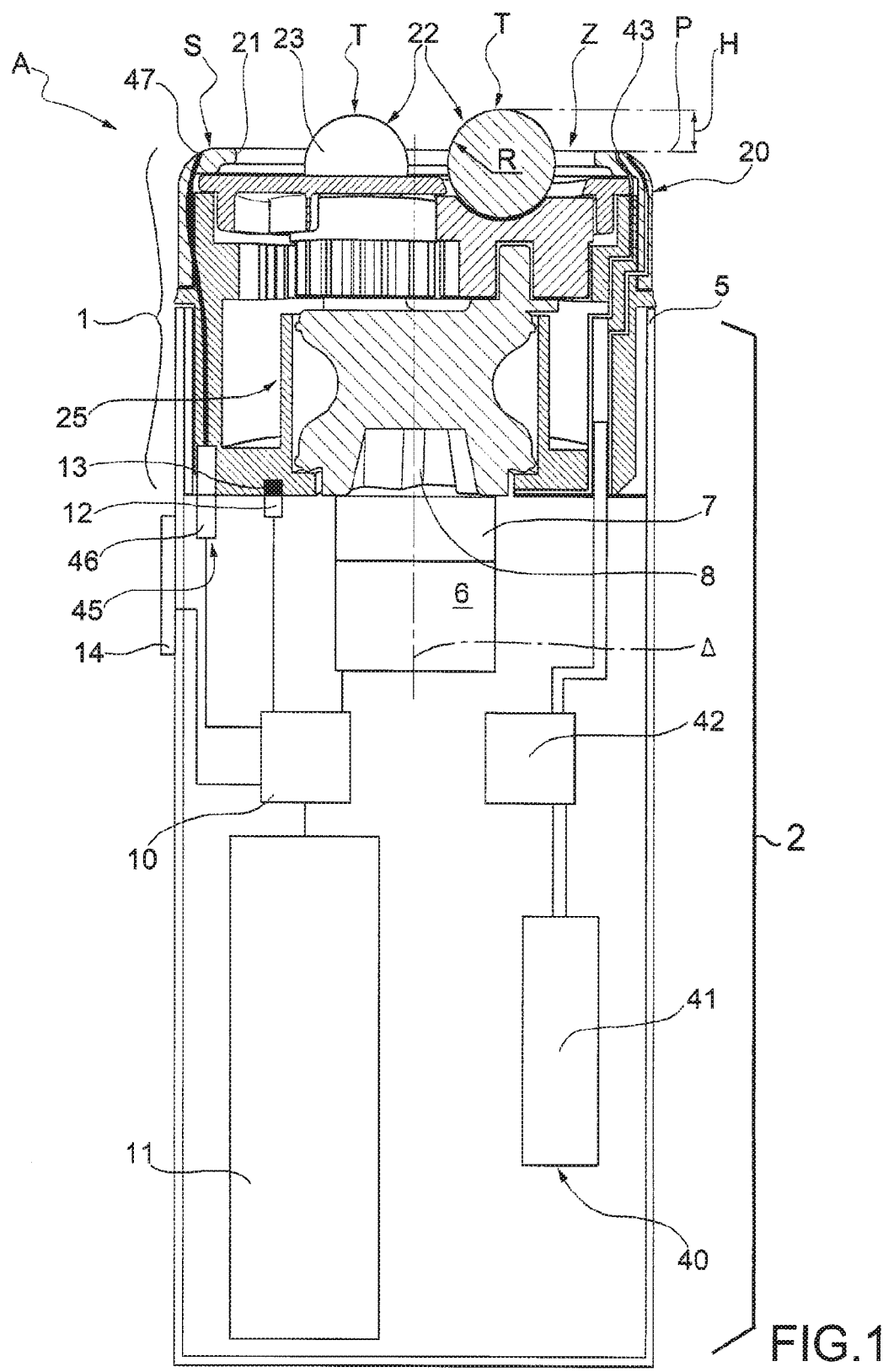
FIG. 1 is a schematic cutaway view of a massage device according to the invention.

A massage device according to the invention, such as the one illustrated in FIG. 1 and designated in its entirety by the reference sign A, comprises a massage head 1 that is removably fitted on a drive housing 2. The massage head 1 is designed to exert a mechanical action on the facial skin of a user by means of massage elements driven by an electric motor.

To this end, the drive housing 2 comprises an elongate body that has the general shape of a cylinder and that comprises means 5 of removably fitting the massage head 1 on one of ends. According to the example shown, the fitting means 5 are formed by a sheath inside which the massage head 1 is partially engaged.

The drive housing 2 comprises, inside the body, an electric motor 6 that actuates drive means 7 designed to transmit the movement of the electric motor to the massage elements of the massage head 1. According to the example illustrated, the drive means 7 comprise a reducing gear (not shown) that drives an output shaft 8 accessible at the fitting means 5 of the drive housing 2.

The electric motor 6 is run by a control unit 10 powered by a battery pack 11 disposed inside the body. Obviously the control unit 10 could also be supplied with electric power directly from the mains by means of a transformer. The control unit 10 is furthermore connected to a manual control interface 14 accessible from the outside of the body. The manual control interface 14 can comprise, for example, an on/off switch and/or means for manually selecting operating programs.

The drive housing 2 also comprises recognition means 12 that are connected to the control unit 10 and that are designed to read identification means 13 carried by the massage head 1. The control unit 10 is thus designed for controlling the functioning of the massage device A on the basis of the massage head 1 as recognized subsequently to the reading of the identification means 13. The controlling of the functioning of the massage device A can consist specifically of determining the rotation speed of the electric motor 6 such that it is adapted to the massage to be performed by the massage elements. The identification means 13 can be composed of, for example, an RFID chip, whereas the recognition means 12 would be designed for reading such an RFID chip. Obviously the identification means 13 and the recognition means 12 could be produced in any other suitable manner such as, for example, in the form of a mechanical or electrical contact identification system, or even in the form of a magnetic identification system employing permanent magnets and reed switches.

Figure 2:
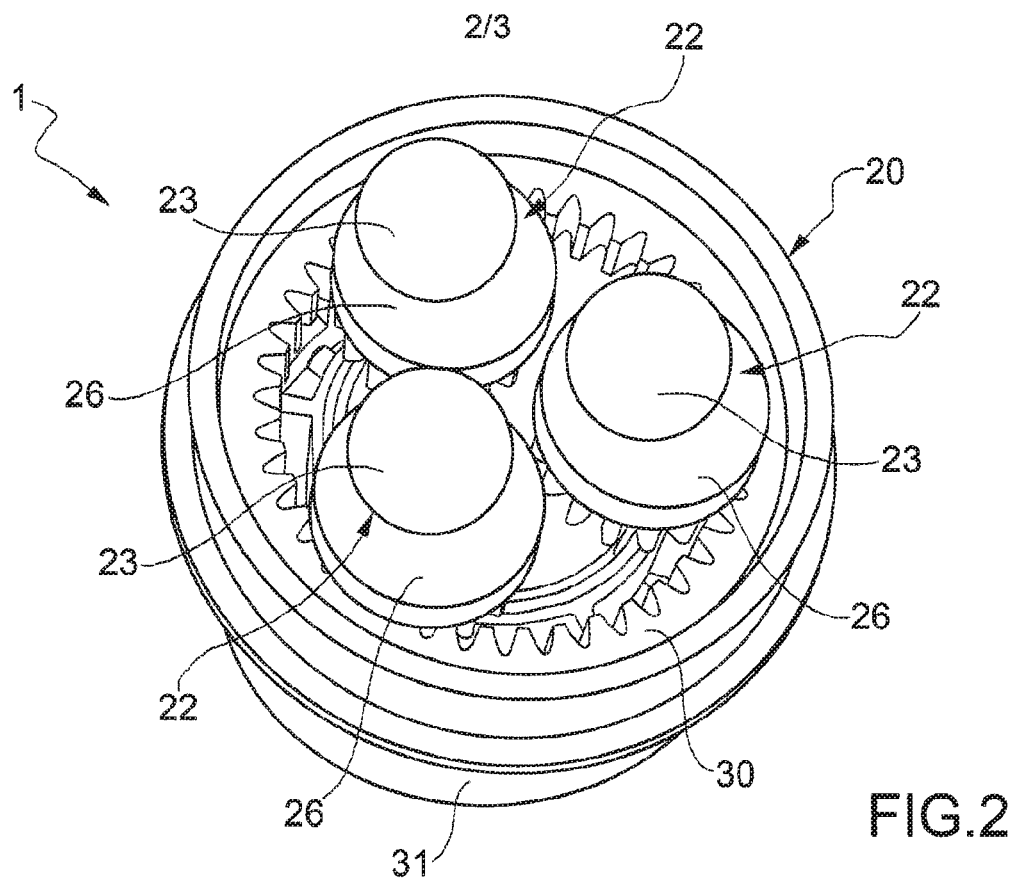
FIG. 2 is perspective view of a first massage head.

According to the invention, the massage head 1 is designed to give a massage by moving a working head against the skin, the head remaining in constant contact with the skin. To this end, the massage head 1 comprises, as shown in FIG. 2, a bearing element 20 that is intended to be placed against the face. The bearing element 20 has an overall annular shape and forms a bearing ring 21 that defines a bearing surface S lying within a bearing plane P, said bearing surface S being designed to fit the skin exactly should the user so desire. According to the illustrated example, the bearing element 20 is hollow and rigid, whereas the bearing surface S is formed by an elastically deformable material such as an elastomer (e.g., silicone or EPDM). Hence the bearing surface S can be deformed by a few millimeters, preferably less than two, in order to fit the shape of the facial region against which it is applied.

The bearing crown 21 delimits a working zone Z, within which, according to the example illustrated, are located at least three working heads 22 that each have a working surface T extending, protruding, from the bearing plane P. According to the example illustrated, each working head 22 comprises a ball 23 such that the corresponding working surface T has a convex and more particularly spherical shape. Each working surface T thus extends, permanently protruding, from the bearing plane P by a height H, which is measured between the top of the working surface T and the bearing plane P and is preferably equal to or greater than the curvature radius R of said ball. According to a variant, the protrusion height H of each working surface T is greater than half the curvature radius R but less than the curvature radius R.

According to the example illustrated, each ball 23 belonging to a working head 22 is made of a rigid material such as metal. Thus each working surface T is rigid as opposed to the flexible or elastically deformable nature of the bearing surface S. In addition, according to this example the surface of each ball 23 is smooth.

According to the invention, the massage head 1 also comprises maneuvering means 25 designed for moving each working head 22 in rotation about an axis Δ that is offset relative to the center of each corresponding working surface T. The maneuvering means 25 are thus designed to cooperate with the drive means 7 and more particularly with the output shaft 8 in such a way as to transmit and transform the rotary motion of the electric motor 6 into a rotary motion of the working heads 22.

Figure 3:
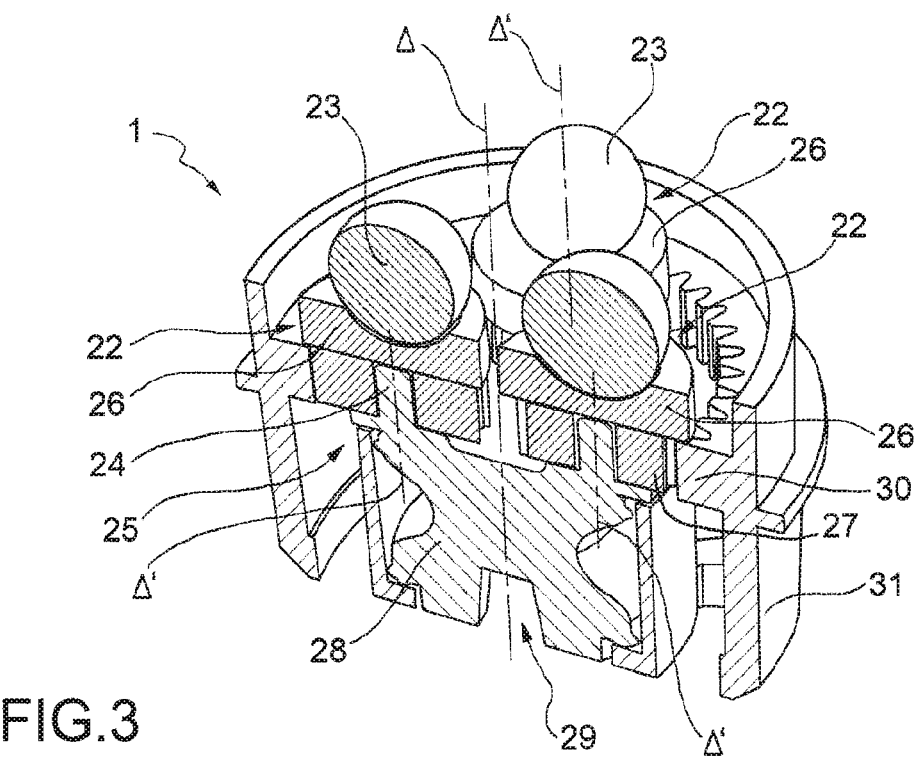
FIG. 3 is a cutaway view of the massage head of FIG. 2.

According to the example illustrated and as can be discerned in FIGS. 2 and 3, the maneuvering means 25 are designed to impart a planetary movement to the three balls 23, in other words a principal movement of the three balls 23 in rotation about the axis of rotation Δassociated with a secondary movement of each of the balls in rotation about a secondary axis of rotation Δ', which moves in rotation about the axis of rotation Δ when the massage device of the invention is in operation.

To this end, each working head 22 comprises a disc 26 that is centered relative to the secondary axis of rotation Δ' and that carries, on its top surface, the corresponding ball 23 rigidly connected to said disc 26. Each working head further comprises a planetary pinion 27 that is rigidly connected to the bottom side of the corresponding disc 26 and that is coaxial with the secondary axis of rotation Δ'.

The maneuvering means 25 thus comprises a maneuvering shaft 28 with an axis Δ, which comprises, on an inner side, a recess 29 for receiving the output shaft 8, and that carries, on a top side, three pins 24 that are each engaged in an axial bore of a planetary pinion 27. The maneuvering means further comprise a fixed ring gear 30 rigidly connected to a constituent casing 31 of the massage head 1. Each of the planetary pinions 27 meshes with the fixed ring gear 30 such that the rotation of the maneuvering shaft 28 brings about the planetary movement of the balls 23 described in the preceding.

In this illustrated variant, it is possible to switch the materials used for the balls and for the bearing ring; in other words, balls made of a flexible material and the ring made of a rigid material.

Depending on the need and with the aim of attenuating the kneading, the massage head 1 can also be constructed in such a way that each working head 22 is mounted on the axis Δ' and executes a uniform rotation on itself.

The massage device thus constructed is employed in the following manner. The bearing surface S is placed against the face, the user then turns the massage device A on via the manual control interface 14, the working heads 22 are thus driven in a planetary rotation movement, whereas the skin around the working zone Z is held by the annular bearing surface S.

The massage performed with the device according to the invention specifically enables a deep kneading of the facial skin, thus smoothing wrinkles by stimulating the circulation and revitalizing the production of the skin's constituent elements.

To optimize this treatment, the massage device A as illustrated in FIG. 1 comprises cosmetic product application means 40. According to the example illustrated, the cosmetic product application means 40 comprise a container 41 located inside the drive housing 2 and connected, via an extraction system 42 such as a pump, to a dispensing nozzle 43 located inside the bearing element 20. The extraction pump 42 is run by the control unit 10 such that cosmetic product is dispensed when the massage device A is in operation. Obviously the bearing element 20 could comprise more than one dispensing nozzle. In addition, each working head could also comprise a cosmetic product distribution nozzle that would be supplied from a flexible container formed in the corresponding working head and actuated by a cam system as said working head rotates.

Furthermore, still according to the example illustrated in FIGS. 1-3, the massage device A also comprises means 45 of applying an electric current, which comprise a unit 46 for generating an electric current and/or voltage. The generator unit 46 is run by the control unit 10. The generator unit 46 is connected to an electrode 47 carried by the bearing element 20.

During the use of the massage device A, the control unit 10 controls the functioning of the generator unit 46 in such a way that when the electrode 47 is in contact with the skin, an electrophoresis phenomenon that enhances the assimilation of the active principles of the cosmetic product is induced.

According to the invention, the working heads 22 are not necessarily driven in a planetary-type movement as described in the preceding.

Figure 4:
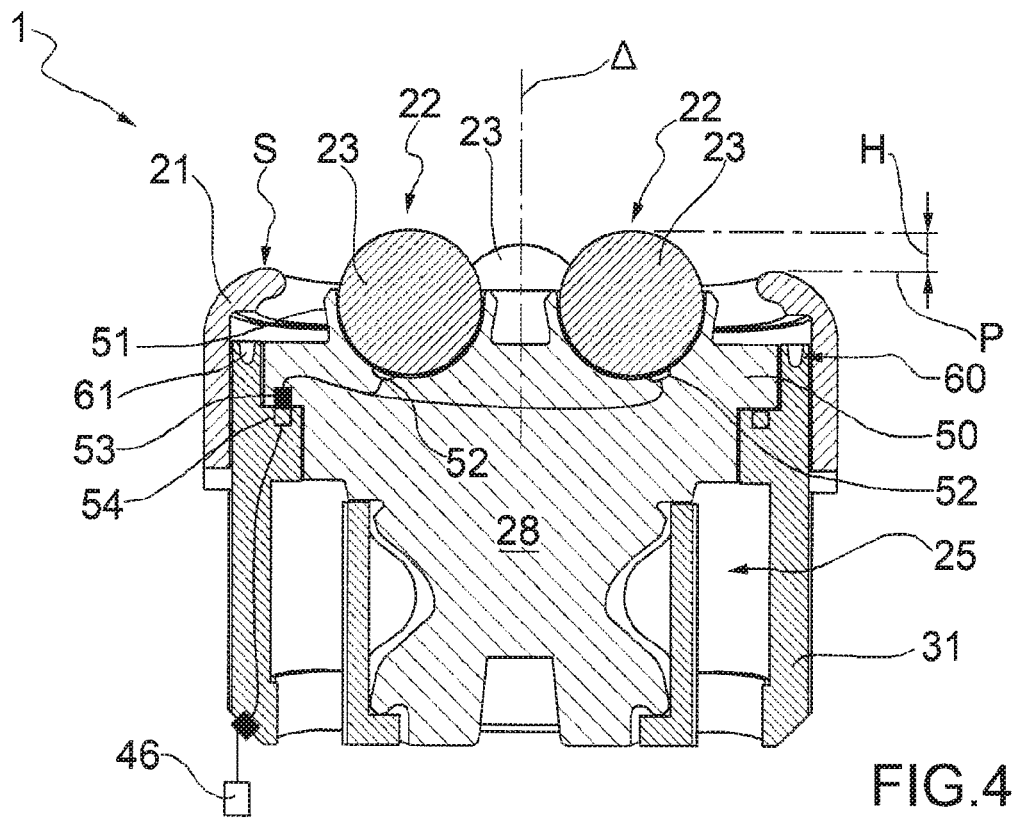
FIG. 4 is a cutaway view of a second massage head.
Figure 5:
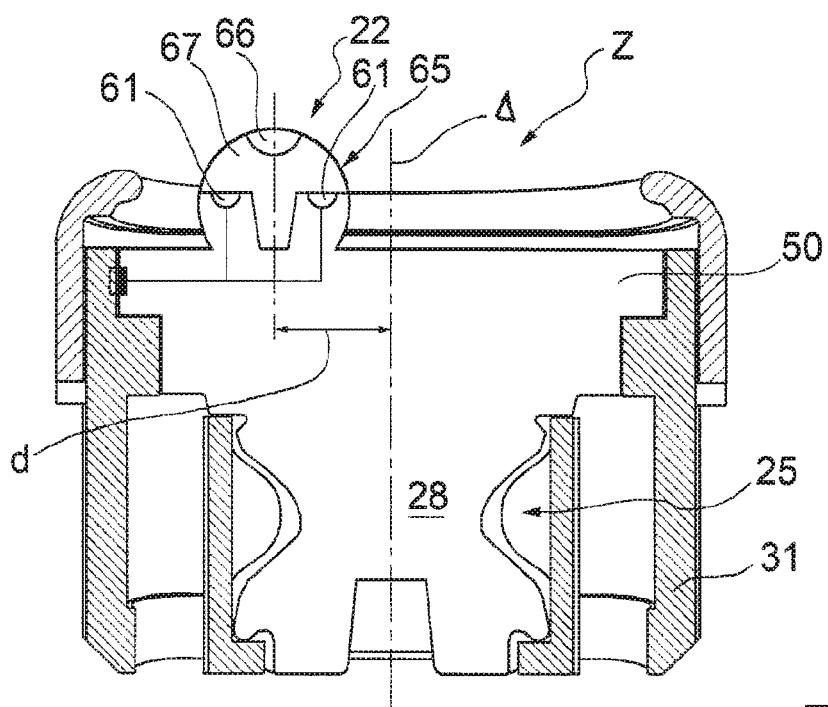
FIG. 5 is a cutaway view of a third massage head.

Accordingly, FIG. 4 illustrates an alternative embodiment of a massage head for a massage device according to the invention that differs from the one described with reference to FIGS. 1-3 in that the three working heads 22 are carried by a circular plate 50 connected in rotation to the maneuvering shaft 28. The plate 50 carries the three working heads 22 formed by the metal balls 23, the centers of which are offset relative to the axis of rotation Δ. Furthermore, the balls 23 are each enclosed in a hemispherical cup 51 rigidly connected to the plate 50. Each ball 23 is thus movable in rotation on itself in such a way that it can roll on the skin when the massage device according to this alternative embodiment is in use.

In addition, according to this exemplary embodiment each working head comprises an electrostimulation electrode that is formed by the corresponding ball 23 and that is electrically connected via a brush 52, 53 and circular track 54 system to the unit 46 for generating a current.

Still according to this exemplary embodiment, the massage head comprises means 60 for diffusing light toward the face. In the present case, the diffusion means 60 are formed in the massage head and, as a light source, comprise light-emitting diodes 61 that are controlled by the control unit 10. The light sources 61 are thus associated with an optical system formed by the bearing element, which is transparent and which comprises a light outlet side located at the bearing surface S and therefore intended to be oriented toward the face of the user of the massage device A according to the invention.

To this end, the entire working zone (Z) can be composed of transparent parts in order to permit the passage of the light.

FIG. 4 illustrates still another alternative embodiment of a massage head 1 of a massage apparatus A of the invention. According to this variant, the massage head 1 only comprises one spherical working head 22 that is rigidly connected to the plate 50 and offset relative to the center thereof. According to this exemplary embodiment, the center of the working head 22 is offset relative to the center of the working zone Z through which the axis Δ passes at a distance d greater than or equal to ⅙ of the smallest dimension of the working zone Z (in this case the diameter of the working zone Z) and less than half of said smallest dimension of the working zone Z.

According to this exemplary embodiment, the working head 22 carries a removable cap 65 that forms a corresponding working surface and comprises a plug 66 on its top that is saturated with cosmetic product. The removable cap 65 thus forms a cosmetic product application means.

According to this exemplary embodiment, the cap 65 further comprises an optical system 67 for diffusing light produced by the light sources 61 located in the working head 22. The optical system 67 in this case is formed by a spherical cap made of transparent material that serves as a light guide.

Obviously, diverse other modifications or variants of the device and of the massage head according to the invention are conceivable within the scope of the appended claims.

The invention claimed is:

1. A facial massage device comprising:
    a massage head, which comprises:
        a bearing element that is intended to be placed against a face and that forms a bearing ring defining a bearing surface (S) lying within a bearing plane (P), and a working zone (Z) located within the bearing ring,
        within the bearing ring and inside the working zone (Z), at least one working head that has at least one working surface that extends, protruding, from the bearing plane (P),
        maneuvering means designed for moving at least one working head in rotation about at least one axis of rotation (Δ, Δ') offset relative to a center of the at least one working surface (T),
        and a drive housing that carries the massage head and that comprises an electric motor actuating drive means designed to transmit a motion of the electric motor to the maneuvering means, wherein the at least one working surface extends, permanently protruding, from the bearing plane (P) by a height H measured between a top of the working surface and the bearing plane P.

2. The massage device according to claim 1, wherein the bearing surface (S) is composed of a first material and that the at least working surface (T) is composed of a second material with a rigidity different from that of the first material, the first material and the second material being chosen from among:
    a rigid material that is non-deformable under a manual force,
    a material that is elastically deformable under a manual force.

3. The massage device according to claim 2, wherein the at least one working surface (T) is composed of an elastically deformable material.

4. The massage device according to claim 1, wherein the at least one working surface (T) has a convex shape.

5. The massage device according to claim 4, wherein the at least one working surface (T) has an essentially spherical shape and extends, wherein the height (H) is equal or greater than a curvature radius (R) of the at least one working surface (T).

6. The massage device according to claim 1, wherein the at least one working head comprises a ball that forms the corresponding working surface (T).

7. The massage device according to claim 6, wherein each ball is movable in rotation on itself.

8. The massage device according to claim 1, wherein the at least one working surface (T) is rigid.

9. The massage device according to claim 1, wherein the at least one working surface (T) is smooth.

10. The massage device according to claim 1, wherein the at least one working surface (T) is metal.

11. The massage device according to claim 1, wherein the at least one working surface (T) is made of a material having a hardness of between 20 and 70 shore.

12. The massage device according to claim 1, wherein the at least one working head of the device is a single working head, a center of which is offset relative to a center of the working zone (Z).

13. The massage device according to claim 12, wherein the center of the single working head is offset relative to the center of the working zone (Z) by a distance (d) greater than or equal to ⅙ of a smallest dimension of the working zone (Z) and less than half of the smallest dimension of the working zone (Z).

14. The massage device according to claim 1, wherein the at least one working head of the device comprises at least two working heads, a center of which is offset relative to a center of the working zone (Z).

15. The massage device according to claim 14, wherein the maneuvering means are designed to move each working head of the at least two working heads in rotation about an axis of rotation (Δ, Δ') offset relative to a center of the at least one working surface (T) and separate from the axis of rotation (Δ, Δ') of the other working head or heads of the at least two working heads.

16. The massage device according to claim 1, wherein the bearing element is hollow and rigid.

17. The massage device according to claim 1, further comprising means of applying an electric current comprising at least one electrode intended to be in contact with the skin and connected to a unit for generating an electric current and/or voltage.

18. The massage device according to claim 17, wherein at least the bearing element or the at least one working head carries at least one electrode.

19. The massage device according to claim 1, further comprising light diffusion means.

20. The massage device according to claim 19, wherein the light diffusion means comprise at least one light source and at least one optical diffusion system comprising an outlet side intended to be oriented toward the face.

21. The massage device according to claim 20, wherein at least the bearing element or the at least one working head comprises a light outlet side.

22. The massage device according to claim 20, wherein at least the bearing element or the working zone is at least partly transparent.

23. The massage device according to claim 1, further comprising means for applying cosmetic product.

24. The massage device according to claim 23, wherein the means for applying cosmetic product comprise at least one cap comprising a plug saturated with cosmetic product and removably fitted on one or both of the bearing element and the at least one working head.

25. The massage device according to claim 23, wherein the means for applying cosmetic product comprise a cosmetic product container and at least one dispensing nozzle connected to a system for extracting the cosmetic product in the container.

26. The massage device according to claim 25, the means for applying cosmetic product comprise at least one dispensing nozzle located in the at least one working head or in the bearing element.

27. The massage device according to claim 1, wherein the massage head is removably fitted on the drive housing.

28. The massage device according to claim 27, wherein the massage head comprises identification means and wherein the drive housing comprises means for recognizing the identification means that are connected to a control unit designed for controlling a functioning of the massage device on a basis of a recognized massage head.

* * * * *

UNITED STATES PATENT AND TRADEMARK OFFICE
CERTIFICATE OF CORRECTION

Page 1 of 1

PATENT NO. : 10,492,980 B2
APPLICATION NO. : 15/029268
DATED : December 3, 2019
INVENTOR(S) : Camille Giraud et al.

It is certified that error appears in the above-identified patent and that said Letters Patent is hereby corrected as shown below:

On the Title Page

Item (72), Column 1, Line 1, delete "Lyons" and insert -- Lyon --

In the Specification

Column 1, Line 8, after "This" insert -- application --

Signed and Sealed this
Second Day of June, 2020

Andrei Iancu
*Director of the United States Patent and Trademark Office*